United States Patent [19]

Mattheck et al.

[11] Patent Number: 5,167,666
[45] Date of Patent: Dec. 1, 1992

[54] ENDOPROSTHESIS FOR THE FEMORAL PART OF A HIP JOINT

[75] Inventors: Claus Mattheck, Leimersheim; Martin Börner, Schwalbach, both of Fed. Rep. of Germany

[73] Assignee: Kernforschungszentrum Karlsruhe GmbH, Karlsruhe, Fed. Rep. of Germany

[21] Appl. No.: 360,904
[22] PCT Filed: Jul. 8, 1988
[86] PCT No.: PCT/DE88/00428
  § 371 Date: May 10, 1989
  § 102(e) Date: May 10, 1989
[87] PCT Pub. No.: WO89/00414
  PCT Pub. Date: Jan. 26, 1989

[30] Foreign Application Priority Data

Jul. 10, 1987 [DE] Fed. Rep. of Germany ....... 3722853

[51] Int. Cl.⁵ .................................................. A61F 2/36
[52] U.S. Cl. ........................................ 623/23; 606/62
[58] Field of Search ...................... 623/23, 22, 18, 16; 606/60-64

[56] References Cited

U.S. PATENT DOCUMENTS

| | | | |
|---|---|---|---|
| 3,781,917 | 1/1974 | Mathys | 623/23 |
| 3,843,975 | 10/1975 | Tronzo | 623/23 |
| 4,516,277 | 5/1985 | Butel | 623/23 |
| 4,698,063 | 10/1987 | Link et al. | 623/23 |
| 4,718,916 | 1/1988 | Morscher | 623/23 |

FOREIGN PATENT DOCUMENTS

| | | | |
|---|---|---|---|
| 0229578 | 7/1987 | European Pat. Off. | 623/23 |
| 0266081 | 5/1988 | European Pat. Off. | 623/22 |
| 2832555 | 2/1980 | Fed. Rep. of Germany | 623/22 |
| 3426947 | 12/1985 | Fed. Rep. of Germany | . |
| 3522692 | 1/1987 | Fed. Rep. of Germany | . |
| 2614524 | 11/1988 | France | 623/23 |
| 1255122 | 9/1986 | U.S.S.R. | 623/23 |

Primary Examiner—David Isabella
Attorney, Agent, or Firm—Spencer, Frank & Schneider

[57] ABSTRACT

An endoprosthesis for a femoral hip joint comprises a stem (1) with a collar (3) which bears against a resected bone surface and has a blocking cone (4) on which the ball head (5) is positioned. A screw (12) which grips the prosthesis as a tensioning stay passes through a lateral bore extending obliquely downward and outward through the femur. The prosthesis stem is designed to permit cementless fixation and to prevent crack formation in the femur due to rigidity of the stem, even under extreme loads. To this end, the prosthesis stem (1) is lodged in a mating fit in a medullary nail (7) driven into the medullary canal, and the distal region of the prosthesis stem (1) is elastic.

8 Claims, 4 Drawing Sheets

ENDOPROSTHESIS FOR THE FEMORAL PART OF A HIP JOINT

BACKGROUND OF THE INVENTION

1. Field of the Invention

The invention relates to an endoprosthesis for the femoral part of a hip joint wherein the prosthesis stem is provided with a prosthesis collar supported on a resected bone surface and with a clamping cone which supports the attachable joint ball. At least one screw which grips the prosthesis in the manner of a tensioning stay passes through a lateral bore, oriented obliquely downward and outward in the femur.

2. Discussion of the Background

A tensioning stay endoprosthesis of the above type is disclosed in German Offenlegungsschrift DE-OS 3,522,692.A1. However, the tensioning screw of the prosthesis stem was already described in the publication "Die Zuggurtung-Hüftendoprothese" [The Tensioning Stay Hip Joint Endoprosthesis], Arch. Orthop. Unfall-Chir. [Archives of Orthopedic Accident Surgery, Vol. 86, (1976) pages 1 to 14. As indicated there, a relatively short stem is driven into the femur (page 11, paragraph 7 and page 9. FIG. 6), since the stem is given only subordinate significance. The stem, which has a broad, medial contact surface and a longitudinal groove, serves only to transmit relatively small forces.

However, for medical technology reasons, the tilting effect occurring in stem-equipped prostheses must not remain unconsidered. Under permanent load, the thick, non-elastic tip of the stem exerts direct pressure against the relatively soft inner wall of the bone. Moreover, the flow of forces must be diverted from the lower end of the prosthesis stem into the bone, thus inducing locally highly concentrated tensions in the bone. This initially results in a constriction of the marrow cavity due to solidification of the spongiosa and in thicker bone walls. Then the tip of the prosthesis stem seats itself on this bone plug in the marrow cavity so that the flow of forces is now directed almost only through the prosthesis into the plug. The result could be regression of the bone wall above the plug and, in the worst case, loosening and breakage of the prosthesis and the bone.

SUMMARY OF THE INVENTION

The invention is based on the object of configuring the just described holding arrangement in such a manner that the prosthesis stem remains seated in the femur without cement and without rigidity cracks even under the greatest stresses.

This is achieved in accordance with the invention by the provision of an endoprosthesis for the femoral part of a hip joint wherein a prosthesis stem is provided with a prosthesis collar supported on a resected bone surface. A clamping cone is attached to the joint ball, with at least one screw engaging the endoprosthesis in the manner of a tensioning stay and passing through a lateral bore in the femur. The bore is oriented obliquely downward and outward. The prosthesis stem is fitted into a hollow marrow nail driven into the leg's marrow cavity. The nail's interior cross sectional dimension corresponds to the cross-sectional dimension of the upper portion of the prosthesis stem. The prosthesis shaft in its distal region is tapered and elastically designed in such a way that any load is transferred evenly over the entire length of the marrow nail onto the femur. Either the prosthesis stem makes contact laterally with the interior of the wall of the marrow nail or the prosthesis stem is designed like a fork having two tines tapered laterally and medially toward the tip.

The particular advantages of the invention are that placement without cement of a comparatively flexible prosthesis stem in a likewise comparatively flexible marrow nail extending into the bottom of the bone prevents, right from the start, the formation of a bone plug and thus a tilting effect. The load is introduced in a manner distributed over the entire length of the nail. In order to additionally stabilize this flexible system, a tension bar is additionally provided on the tension side, laterally outwardly. The significant novelty is thus the combination of a prosthesis stem and a marrow nail.

DETAILED DESCRIPTION OF THE PREFERRED EMBODIMENTS

Figure 1:
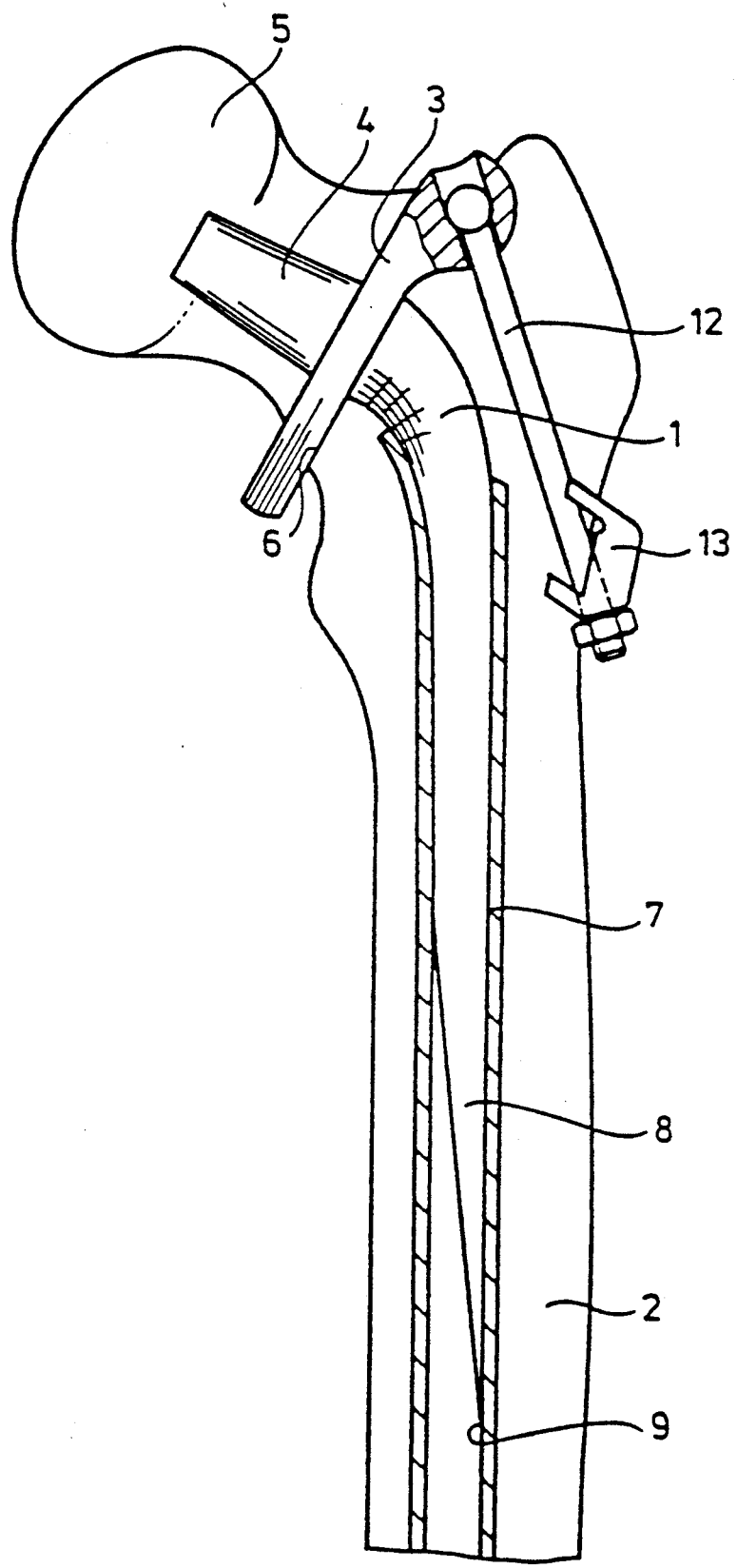
FIG. 1 is an elevational view, in partial section, of a bone fitted with an endoprosthesis according to the present invention.

For all three embodiments (FIGS. 1 to 3) the endoprosthesis for the femoral part of a hip joint includes a curved stem 1 which is to be held in a tubular bone 2. The stem continues in the form of a prosthesis collar 3 and a clamping cone 4 which accommodates a joint ball 5. Prosthesis collar 3 is seated on a planar resected surface 6.

Figure 4:
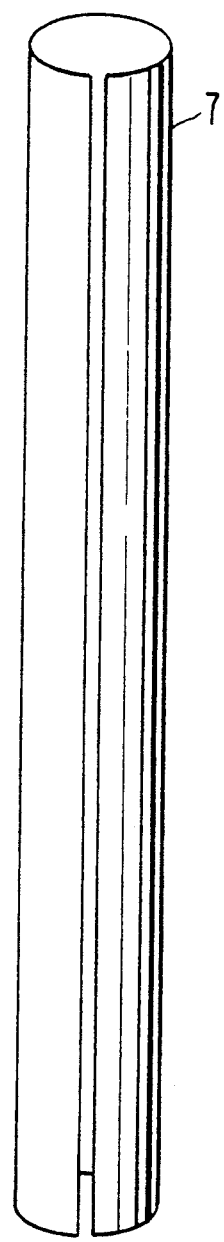
FIG. 4 is a side view of a hollow marrow nail which is slotted over its entire length.

Before insertion of prosthesis stem 1, a marrow nail 7 is introduced into femur 2 according to the invention. This nail is hollow, preferably slotted to its end (see FIG. 4) and extends over the entire length of femur 2 and its marrow cavity. The cross-sectional dimensions of marrow nail 7 are adapted, at least at its upper end, to the dimensions of the upper portion of the stem to be inserted. The free stem end 8, however, is flexible. Advantageously, the interior profile of the nail is circular.

According to the embodiment of FIG. 1, stem end 8 ends in a point (is tapered) toward the region remote from the joint and comes to lie against the lateral interior face 9 of marrow nail 7. Implantable steel, as well as bonded fibers, are suitable as the material.

Figure 2:
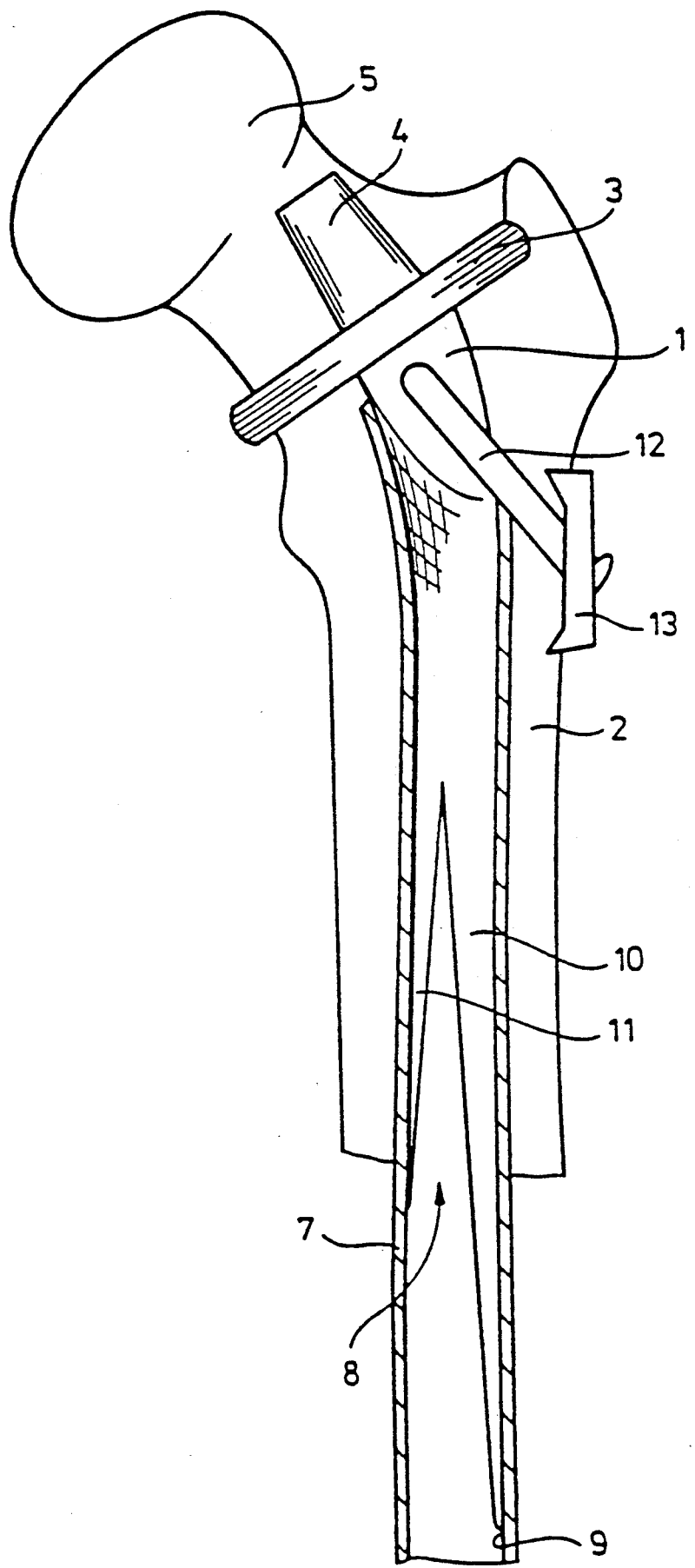
FIG. 2 is an elevational view, in partial section, of a bone fitted with an alternative embodiment endoprosthesis according to the present invention.
Figure 3:
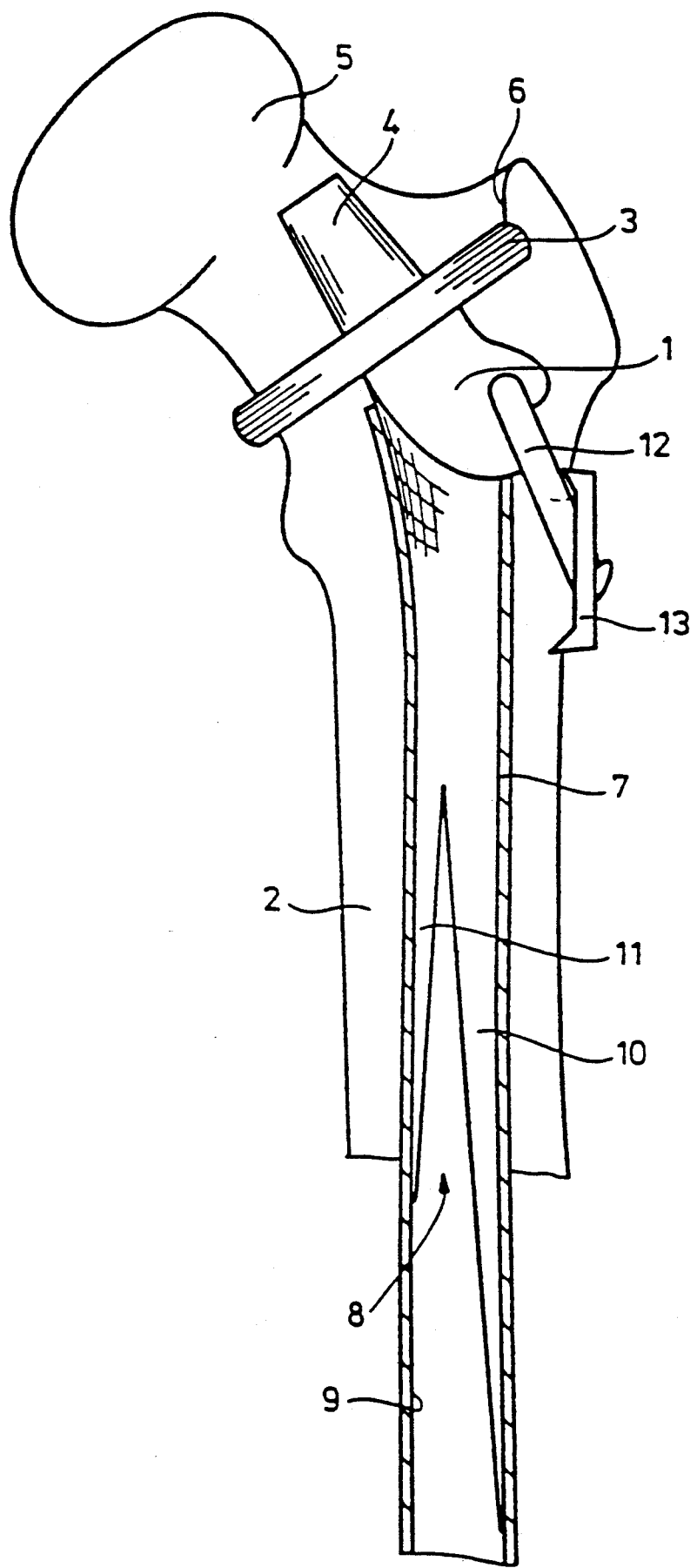
FIG. 3 is an elevational view, in partial section, of a bone fitted with a second alternative embodiment endoprosthesis according to the present invention.

According to the illustrations of FIGS. 2 and 3, the stem end 8 is given a bifurcated shape. Two tines 10 and 11 which are tapered toward the tip are provided in each case, with the somewhat shorter tine (11) lying medially against interior wall 9 and the longer tine (10) lying laterally against interior wall 9. This bifurcation increases the elasticity of stem end 8 and distributes the load over the entire marrow nail length from where it is transferred to the femur 2.

In all three embodiments, a tension anchor is additionally provided. For this purpose, at least one screw 12, e.g. a corticalis screw or a conventional screw having metal threads which are fixed in a lateral receiving plate, is provided or a bar equipped with a serrated disc 13, respectively. The screw or bar extends through femur 2 and is fastened either to prosthesis collar 3 (FIG. 1) or below prosthesis collar 3 to stem 1 within the axis (FIG. 2) or outside the axis (FIG. 3). Further fastening elements, e.g. locking nails may be provided for marrow nail 7.

We claim:

1. Endoprosthesis for a femur comprising:

an elongated hollow marrow nail, defining interior and exterior surfaces, for insertion into the marrow cavity of a resected femur;

a prosthesis including a stem having a proximal portion and an elastic distal portion, said distal portion being tapered and configured to be inserted into said marrow nail to provide lateral contact along the interior surface for transferring applied forces evenly over the entire length of said marrow nail, said marrow nail having an interior cross-sectional dimension which is complimentary to a cross sectional dimension of at least an upper end of the distal portion of the stem;

a collar affixed to the proximal portion of the stem, said collar having a radially extending bone engaging surface for being supported on the resected femur surface, said collar including a clamping cone adapted for carrying a joint element; and a tension bar configured to pass through at least one obliquely downwardly and outwardly oriented lateral bore formed in the femur, said tension bar including engagement means for engaging one of said collar or said proximal portion of said stem just below said collar for anchoring the stem to the femur.

2. Endoprosthesis for a femur comprising:

an elongated hollow marrow nail, defining interior and exterior surfaces, for insertion into the marrow cavity of a resected femur;

a prosthesis including a stem having a proximal portion and an elastic distal portion, said distal portion being fork-shaped including two tapered tines and configured to be inserted into said marrow nail to provide lateral contact along the interior surface for transferring applied forces evenly over the entire length of said marrow nail, said marrow nail having an interior cross-sectional dimension which is complimentary to a cross sectional dimension of at least an upper end of the distal portion of the stem;

a collar affixed to the proximal portion of the stem, said collar having a radially extending bone engaging surface for being supported on the resected femur surface, said collar including a clamping cone adapted for carrying a joint element; and a tension bar configured to pass through at least one obliquely downwardly and outwardly oriented lateral bore formed in the femur, said tension bar including engagement means for engaging one of said collar or said proximal portion of said stem just below said collar for anchoring the stem to the femur.

3. The endoprosthesis as defined in claim 2, wherein said tension bar means comprises a screw engaging said collar.

4. The endoprosthesis as defined in claim 1, wherein said tension bar comprises a screw engaging said stem just below said collar.

5. The endoprosthesis as defined in claim 1, wherein said marrow nail is slotted over its entire length.

6. The endoprosthesis as defined in claim 2, wherein said tension bar means comprises a screw engaging at said collar.

7. The endoprosthesis as defined in claim 2, wherein said tension bar comprises a screw engaging said stem just below said collar.

8. The endoprosthesis as defined in claim 2, wherein said marrow nail is slotted over its entire length.

* * * * *